(12) United States Patent
Takahashi

(10) Patent No.: US 8,545,389 B2
(45) Date of Patent: Oct. 1, 2013

(54) OPERATING FIELD SECURING DEVICE

(75) Inventor: Seiya Takahashi, Chofu (JP)

(73) Assignee: Olympus Corporation, Tokyo (JP)

( * ) Notice: Subject to any disclaimer, the term of this patent is extended or adjusted under 35 U.S.C. 154(b) by 569 days.

(21) Appl. No.: 12/533,619

(22) Filed: Jul. 31, 2009

(65) Prior Publication Data

US 2009/0299132 A1 Dec. 3, 2009

Related U.S. Application Data

(63) Continuation of application No. PCT/JP2008/051561, filed on Jan. 31, 2008.

(30) Foreign Application Priority Data

Feb. 1, 2007 (JP) .................................. 2007-023306

(51) Int. Cl.
*A61F 2/00* (2006.01)

(52) U.S. Cl.
USPC .......................................................... 600/37

(58) Field of Classification Search
USPC .................... 600/16–18, 37, 232; 606/167
See application file for complete search history.

(56) References Cited

U.S. PATENT DOCUMENTS

| | | | |
|---|---|---|---|
| 6,331,157 B2 | 12/2001 | Hancock | |
| 6,939,297 B2 | 9/2005 | Gannoe et al. | |
| 6,994,669 B1 | 2/2006 | Gannoe et al. | |
| 2001/0023311 A1* | 9/2001 | Snow | 600/37 |
| 2001/0037123 A1 | 11/2001 | Hancock | |
| 2002/0016527 A1 | 2/2002 | Hancock | |
| 2002/0077532 A1 | 6/2002 | Gannoe et al. | |

FOREIGN PATENT DOCUMENTS

| | | |
|---|---|---|
| JP | 2001-61860 | 3/2001 |
| JP | 2002-345839 | 12/2002 |
| JP | 2003-521296 | 7/2003 |

* cited by examiner

*Primary Examiner* — Christine Matthews
(74) *Attorney, Agent, or Firm* — Scully, Scott, Murphy & Presser, P.C.

(57) ABSTRACT

An operating field securing device is configured as follows. Namely, An operating field securing device which secures an operating field when an internal organ is subjected to a predetermined procedure, the operating field securing device including a contact portion which comes in contact with the internal organ, and a manipulator holding portion which fixes the relative positions of the internal organ and a manipulator portion to subject the internal organ to the predetermined procedure, thereby holding the manipulator portion.

2 Claims, 6 Drawing Sheets

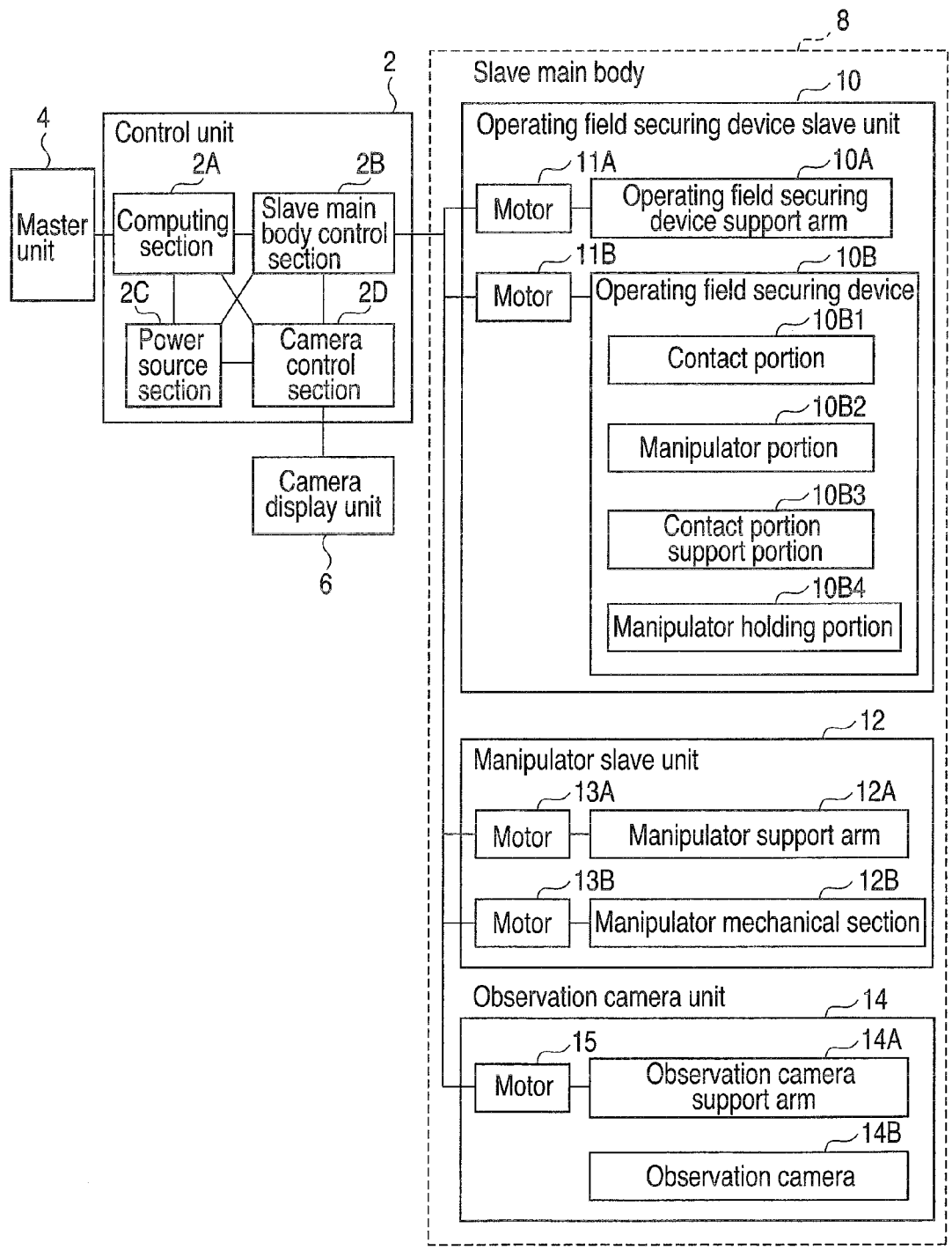
F I G. 2

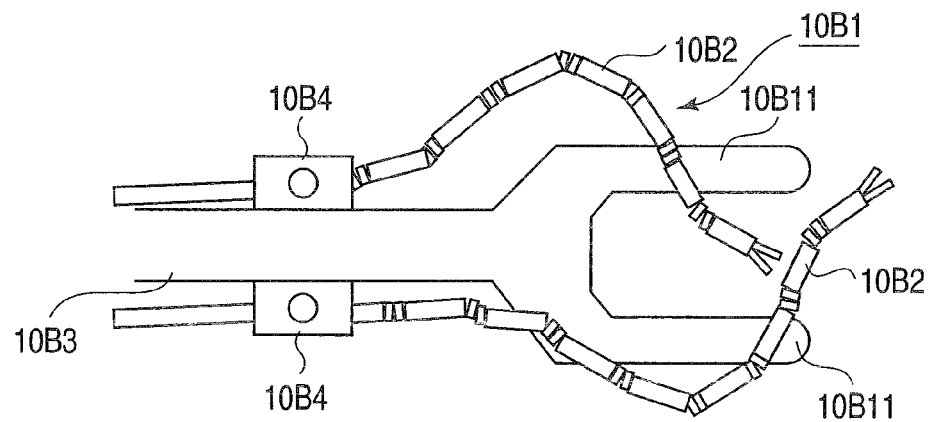
F I G. 3A
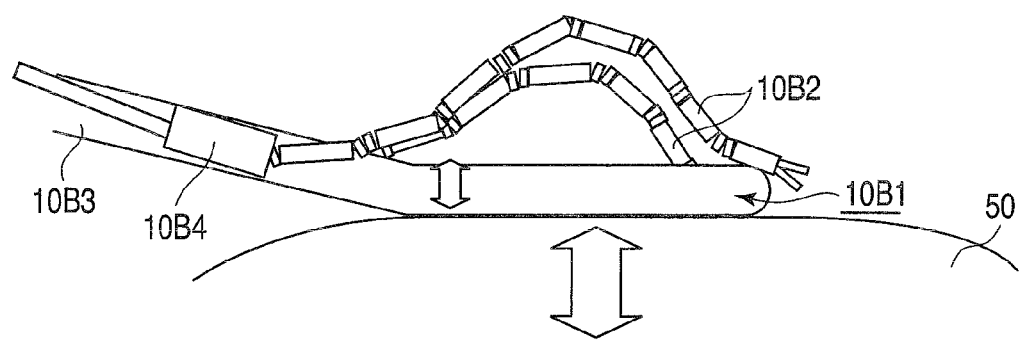
F I G. 3B

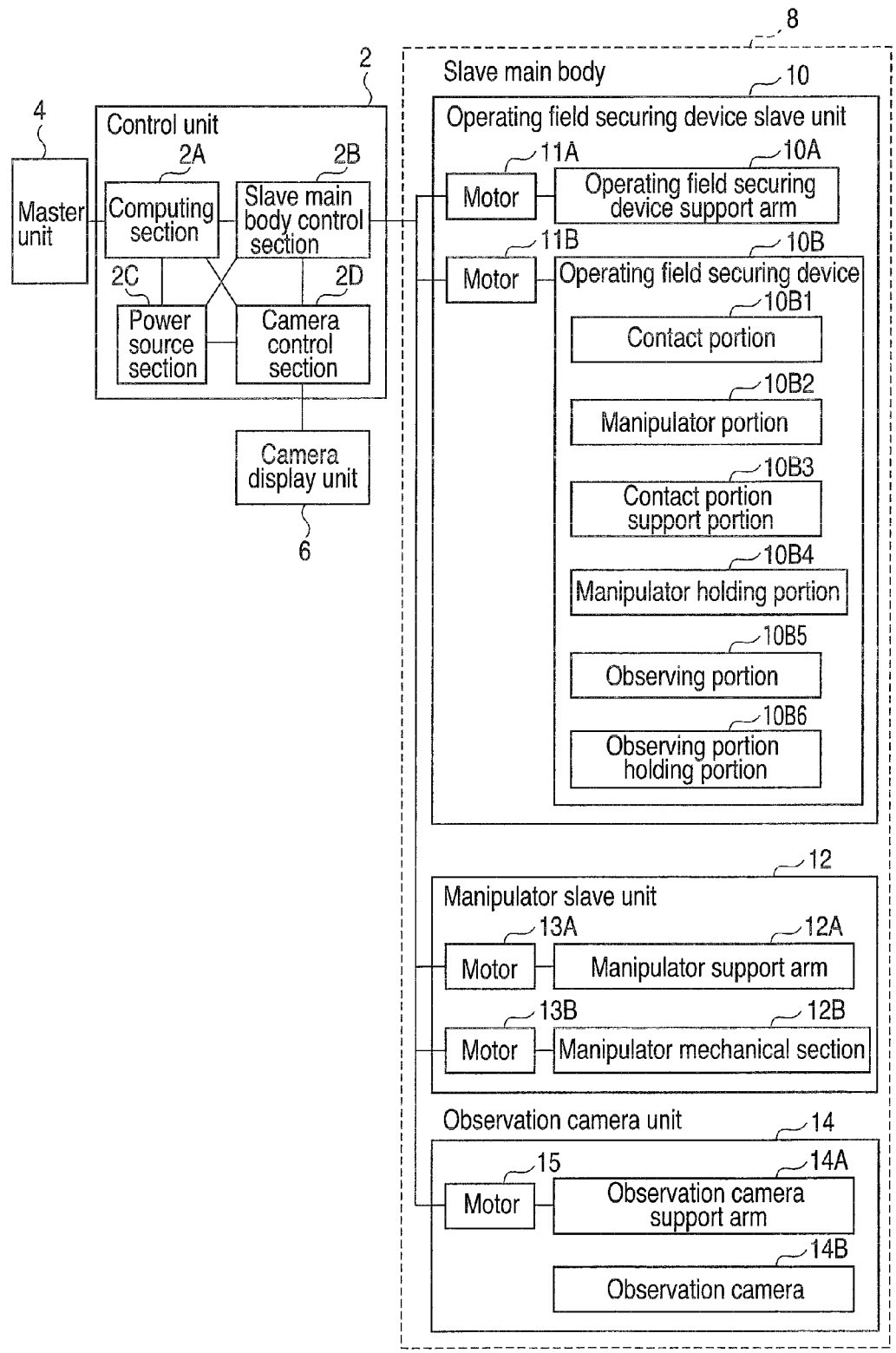
F I G. 5

OPERATING FIELD SECURING DEVICE

CROSS-REFERENCE TO RELATED APPLICATIONS

This is a Continuation Application of PCT Application No. PCT/JP2008/051561, filed Jan. 31, 2008, which was published under PCT Article 21(2) in Japanese.

This application is based upon and claims the benefit of priority from prior Japanese Patent Application No. 2007-023306, filed Feb. 1, 2007, the entire contents of which are incorporated herein by reference.

BACKGROUND OF THE INVENTION

1. Field of the Invention

The present invention relates to an operating field securing device which comes into contact with an internal organ such as the heart to perform various procedures and the like during surgery on the internal organ.

2. Description of the Related Art

In conventional cardiac surgery, the chest cavity is accessed by incising a breast bone (median breast bone incision). Moreover, when the chest cavity is accessed as described above, a retractor is disposed at a position of the breast to be incised, and the breast bone and tissue are spread by the retractor, thereby forming a large opening. Then, a surgical instrument is disposed through the opening to perform the cardiac surgery.

Meanwhile, one of the most general types of cardiac surgery is coronary artery bypass grafting (CABG). In CABG, when one or a plurality of coronary arteries are blocked, the coronary artery on the downstream side of this blockage is connected to a transplanted blood vessel (hereinafter referred to as the graft) to provide a bypass.

A technology for connecting the graft to the coronary artery in this manner is known as anastomasis. As the above graft, for example, a thoracic artery incised from a chest wall is used. In this case, the upstream end of the thoracic artery is left undamaged, and the downstream end of the thoracic artery is connected to the coronary artery.

Moreover, as the graft; an artery or a vein from any part of a patient's body may be used. Furthermore, an artificial blood vessel graft may be used as the graft. In this case, the upstream end of the graft is connected to an artery such as an aorta, and the downstream end thereof is connected to the coronary artery. As described above, a plurality of blocked coronary arteries at various positions of the front, side and back of the heart are bypassed by using a plurality of grafts.

It is to be noted that CABG is performed while the patient's heart is stopped. Therefore, the patient's blood is circulated by using an artificial heart-lung device. However, CABG may be performed by using a technology known as "off-pump coronary artery bypass" (OPCAB) while the heart is beating. That is, the use of the artificial heart-lung device can be avoided owing to OPCAB.

In OPCAB, while the heart is beating, the surface of the heart near the region of the coronary artery to be anastomosed is fixed by using a special instrument referred to as a stabilizer. Since the surface of the heart is locally fixed by this stabilizer, the region to be anastomosed is kept to be as immobile as possible while the graft is connected to the coronary artery.

Here, the stabilizer includes, for example, a contact portion which comes in contact with the surface of an internal organ, and a flexible contact portion support portion for supporting the contact portion. The contact portion support portion is constituted of a plurality of joining members so that the contact portion support portion can be bent or deformed.

Moreover, an elongated cable such as a wire is extended through the joining members. The tension of this cable is appropriately regulated to bend or deform the contact portion support portion, thereby inserting the contact portion support portion into the chest cavity. Then, the contact portion is brought into contact with a target region of the surface of the heart in the chest cavity, and the surface of the heart is pressed or adsorbed by the contact portion to suppress the vibration of the heart. Since the vibration of the heart is suppressed in this manner, an operating field securing device including a manipulator for performing various surgical procedures can be used to accurately operate on the heart. It is to be noted that the above technology concerning the stabilizer is disposed in, for example, Japanese Patent Publication No. 2003-521296.

BRIEF SUMMARY OF THE INVENTION

To achieve the above object, a first aspect of the present invention is directed to an operating field securing device which secures an operating field when an internal organ is subjected to a predetermined procedure, characterized by including a contact portion which comes in contact with the internal organ; and a manipulator holding portion which fixes the relative positions of the internal organ and a manipulator portion to subject the internal organ to the predetermined procedure, thereby holding the manipulator portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram showing one example of a control system constitution of the surgical master/slave system to which the operating field securing device according to the embodiment of the present invention is applied;

FIG. 3A is a diagram of the operating field securing device according to the embodiment of the present invention vertically from a part above the surface to be pressed by a contact portion (from the side of the top surface of the device);

FIG. 3B is a diagram of the operating field securing device according to the embodiment of the present invention, while pressing the heart, from the side of the side surface of the device;

FIG. 5 is a block diagram showing one example of a control system constitution of the surgical master/slave system shown in FIG. 4;

DETAILED DESCRIPTION OF THE INVENTION

Hereinafter, one embodiment of the present invention will be described with reference to the drawings.

Figure 1:
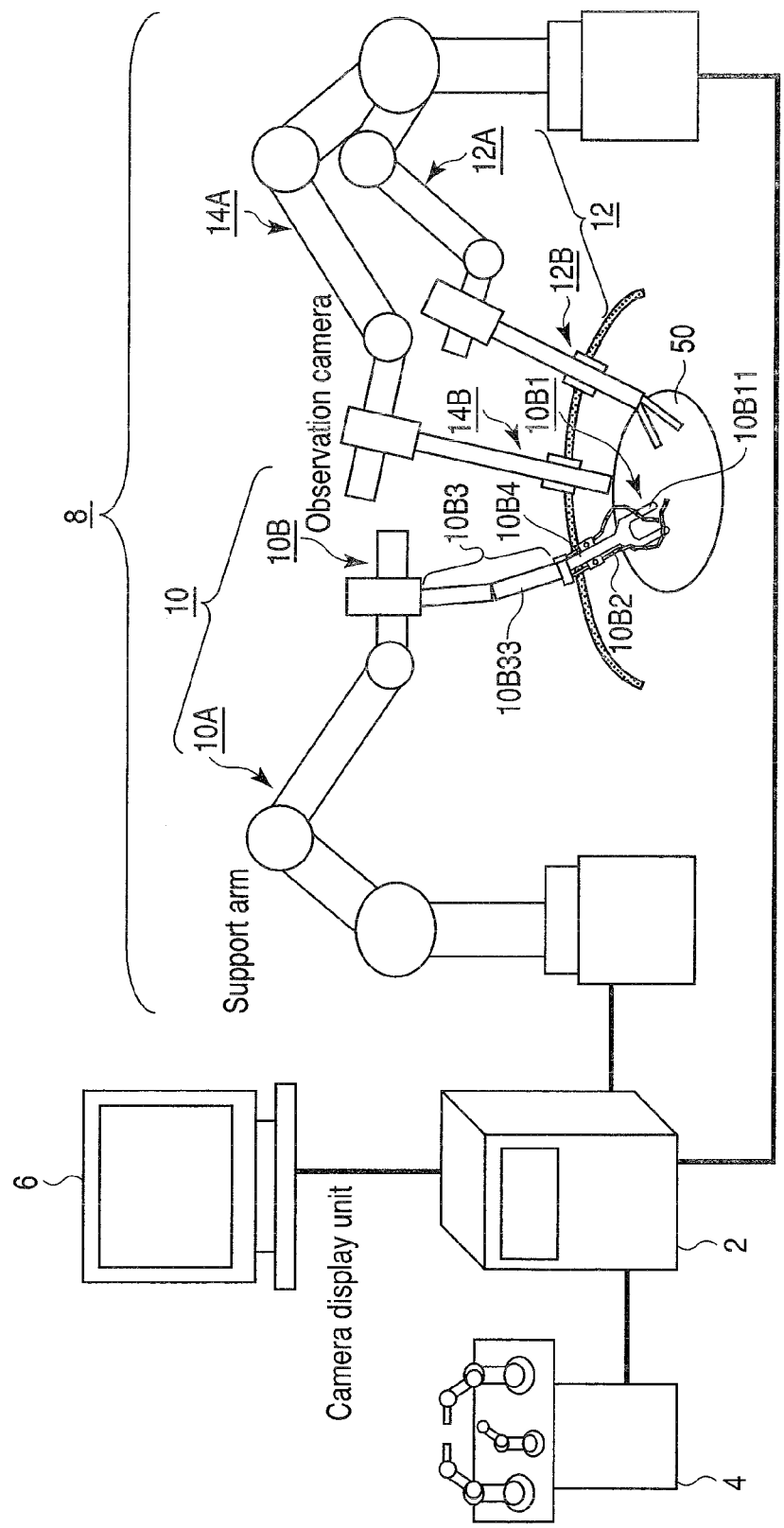
FIG. 1 is a diagram showing one constitution example of a surgical master/slave system to which an operating field securing device according to one embodiment of the present invention is applied.

FIG. 1 is a diagram showing one constitution example of a surgical master/slave system to which an operating field securing device according to one embodiment of the present invention is applied. FIG. 2 is a block diagram showing a control system constitution of the surgical master/slave system shown in FIG. 1.

As shown in FIGS. 1 and 2, the surgical master/slave system, to which the operating field securing device according to the present embodiment is applied, includes a control unit 2, a master unit 4, a camera display unit 6, and a slave main body 8 including the operating field securing device according to the present embodiment.

The control unit 2 has a computing section 2A which performs computation for performing the operational control of parts described later in the slave main body 8 based on the user's operation of the master unit 4; a slave main body control section 2B which performs the operational control of the slave main body 8 based on a computation result obtained by the computing section 2A; a power source section 2C for supplying power sources to the control unit 2, the master unit 4, the camera display unit 6 and the slave main body 8, respectively; and a camera control section 2D which controls an observation camera unit 14 of the slave main body 8 and which controls the display of an image acquired by the observation camera unit 14 in the camera display unit 6.

The master unit 4 converts the user's operation of the master unit 4 into position/posture information to output the information to the computing section 2A of the control unit 2.

The camera display unit 6 outputs and displays the image photographed and acquired by the observation camera unit 14 of the slave main body 8.

Moreover, the slave main body 8 has an operating field securing device slave unit 10 including the operating field securing device (described later in detail) according to the present embodiment; a manipulator slave unit 12 for performing various procedures with respect to an internal organ (hereinafter the heart is assumed as the internal organ) 50 and the like; and the observation camera unit 14 which photographs and acquires the image of a region to be operated on by the manipulator slave unit 12 or the like.

The operating field securing device slave unit 10 includes an operating field securing device support arm section 10A for supporting an operating field securing device mechanical section 10B described later and moving the operating field securing device mechanical section 10B to a user's desired position by the control of the slave main body control section 2B; a motor 11A which drives the operating field securing device support arm section 10A; the operating field securing device mechanical section 10B (the detailed constitution thereof will be described later) according to the present embodiment; and a motor 11B for operating the operating field securing device mechanical section 10B by the control of the slave main body control section 2B.

Hereinafter, the detailed constitution of the operating field securing device mechanical section 10B as one of main characteristic sections of the present embodiment will be described with reference to FIGS. 1 to 3B. FIG. 3A is a diagram of the operating field securing device mechanical section 10B vertically from a part above a contact surface to be contacted by a contact portion 10B1 (from the side of the top surface of the section). FIG. 3B is a diagram of the operating field securing device mechanical section 10B pressing the heart 50, from the side of the side surface of the section.

First, as shown in FIGS. 1 and 2, the operating field securing device mechanical section 10B includes the contact portion 10B1 which comes in contact with the heart 50; a manipulator portion 10B2 for performing various procedures with respect to the heart 50; a contact portion support portion 10B3 which supports the contact portion 10B1; and a manipulator holding portion 10B4 which holds the manipulator portion 10B2 with respect to the contact portion support portion 10B3 so that the manipulator portion 10B2 and the heart 50 synchronously vibrate.

Here, in the present embodiment, the shape of the contact portion 10B1 is a U-shape including two tip portions 10B11 as shown in FIGS. 1 and 3.

More specifically, the contact portion support portion 10B3 is constituted of a plurality of joining members 10B33 so that the contact portion support portion 10B3 can be bent or deformed. An elongated cable (not shown) such as a wire extends through this joining members 10B33. The tension of this cable is appropriately regulated to bend or deform the contact portion support portion 10B3, thereby inserting the contact portion support portion 10B3 into a chest cavity. Then, in the chest cavity, the contact portion 10B1 is brought into contact with a target region of the surface of the heart 50. The contact portion 10B1 is brought into contact in this manner to vibrate in synchronization with the vibration of the heart 50.

Here, the manipulator holding portion 10B4 fixes the manipulator portion 10B2 with respect to the contact portion support portion 10B3.

Moreover, since the contact portion support portion 10B3 is a member to support the contact portion 10B1, needless to say, the contact portion support portion 10B3 and the contact portion 10B1 synchronously vibrate. Therefore, needless to say, the manipulator portion 10B2 having one end thereof being fixed to the manipulator holding portion 10B4 fixed to the contact portion support portion 10B3 vibrates synchronously with the heart 50. Consequently, a relative positional relation between the manipulator portion 10B2 and the heart 50 is constantly fixed. It is to be noted that even when the manipulator holding portion 10B4 is not fixed to the contact portion support portion 10B3 but is fixed to the contact portion 10B1, a similar effect can be obtained.

Since the manipulator portion 10B2 and the heart 50 synchronously vibrate, the relative positional relation between the manipulator portion 10B2 and the heart 50 does not change. Consequently, even when the vibration of the heart 50 cannot completely be suppressed by a stabilizer or the like, the heart 50 can be subjected to a desired procedure by the manipulator portion 10B2 regardless of the vibration of the heart 50.

Meanwhile, the manipulator slave unit 12 includes a manipulator support arm portion 12A which supports a manipulator mechanical section 12B described later and which moves the manipulator mechanical section 12B to a users desired position by the control of the slave main body control section 2B; a motor 13A which drives the manipulator support arm portion 12A; the manipulator mechanical section 12B which performs a desired procedure with respect to the heart 50; and a motor 13B which operates the manipulator mechanical section 12B by the control of the slave main body control section 2B.

It is to be noted that the manipulator slave unit 12 is not associated with the characteristic part of the present invention, and hence the detailed description thereof is omitted.

Moreover, the observation camera unit 14 includes an observation camera support arm section 14A which supports an observation camera 14B described later and which moves the observation camera 14B to a user's desired position by the control of the slave main body control section 2B; a motor 15 which drives the observation camera support arm section 14A; and the observation camera 14B which photographs and acquires an image for observing a region where the heart 50 is pressed by the operating field securing device slave unit 10, a region where the heart 50 is operated on by the manipulator slave unit 12 or the like.

It is to be noted that the observation camera unit 14 is not associated with the characteristic part of the present invention, and hence the detailed description thereof is omitted.

As described above, according to the present embodiment, there can be provided the operating field securing device which subjects the internal organ to various procedures and which can accurately subject the internal organ to various procedures without being influenced by the vibration of the internal organ.

The present invention has been described above with respect to one embodiment, but the present invention is not limited to the above embodiment and, needless to say, the present invention can variously be modified and applied without departing from the scope of the present invention as in, for example, a modification described later.

[Modification]

Figure 4:
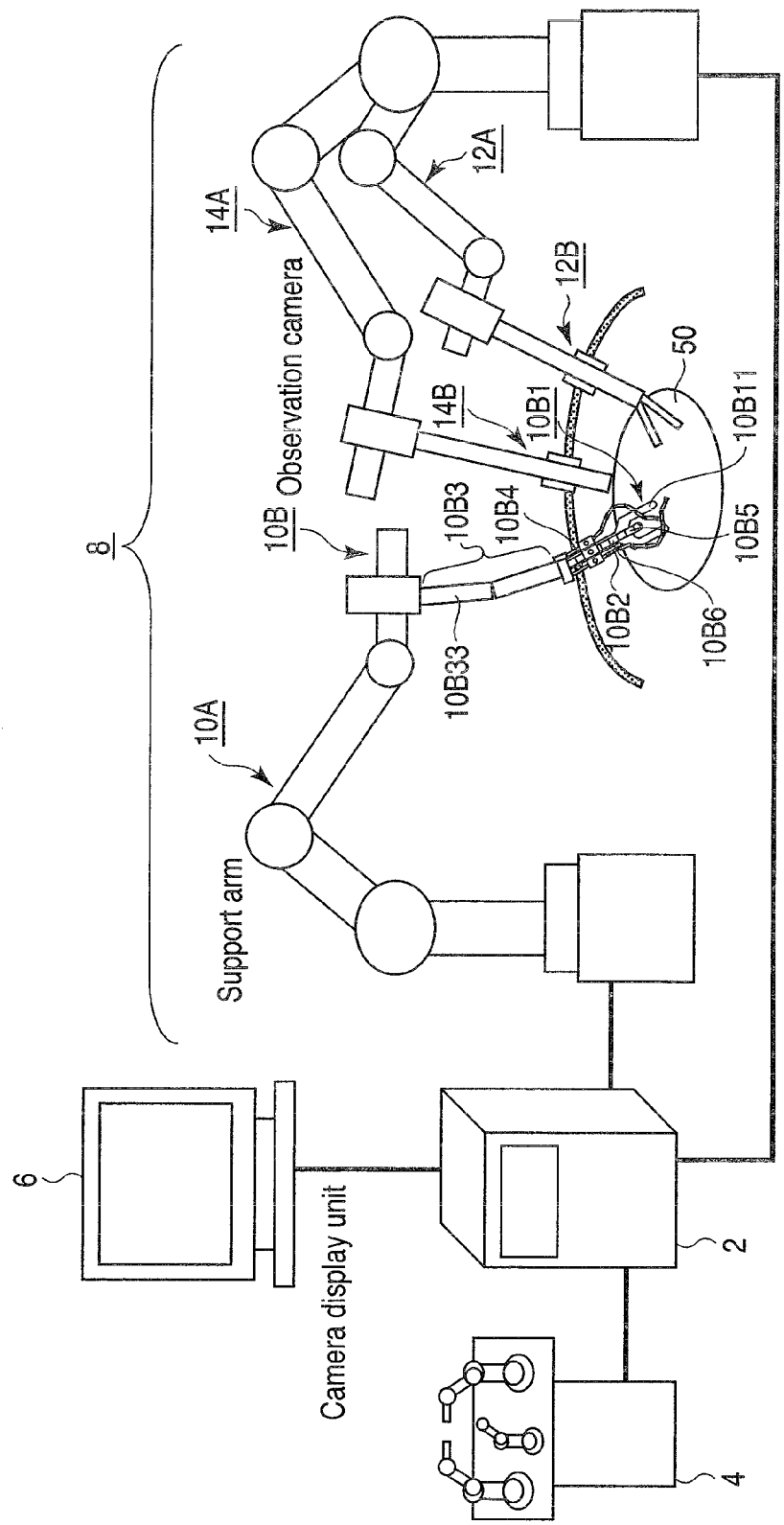
FIG. 4 is a diagram showing one constitution example of a surgical master/slave system to which an operating field securing device according to one modification is applied.
Figure 6A:
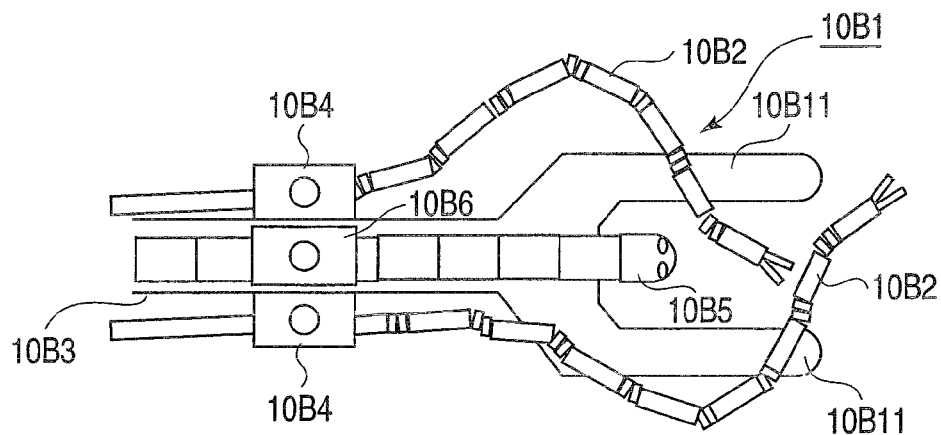
FIG. 6A is a diagram of an operating field securing device mechanical section according to the modification vertically from a part above a contact surface to be contacted by a contact portion (from the side of the top surface of the section)
Figure 6B:
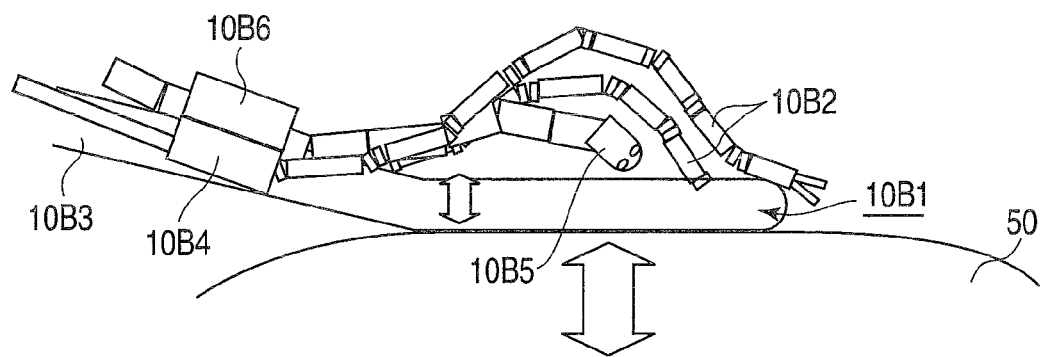
FIG. 6B is a diagram of the operating field securing device mechanical section according to the modification, while pressing the heart, from the side of the side surface of the section.

FIG. 4 is a diagram showing one constitution example of a surgical master/slave system to which an operating field securing device according to the present modification is applied. FIG. 5 is a block diagram showing one example of a control system constitution of the surgical master/slave system shown in FIG. 4. FIG. 6A is a diagram of an operating field securing device mechanical section 10B according to the present modification vertically from a part above a surface to be pressed by a contact portion 10B1 (from the side of the top surface of the section). FIG. 6B is a diagram of the operating field securing device mechanical section 10B according to the present modification, while pressing a heart 50, from the side of the side surface of the section.

That is, as shown in FIGS. 4 to 6B, the operating field securing device mechanical section 10B may further be provided with an observing portion 10B5 for photographing a region or the like subjected to various procedures by the manipulator portion 10B2; and an observing portion holding portion 10B6 which holds the observing portion 10B5 in the contact portion support portion 10B3 so that the observing portion 10B5 and the heart 50 synchronously vibrate.

Here, as shown in FIGS. 6A, 6B, the observing portion 10B5 is fixed to the contact portion support portion 10B3 by the observing portion holding portion 10B6. Here, the observing portion holding portion 10B6 is a member which supports the contact portion 10B1 as described above, and vibrates synchronously with the contact portion 10B1. There-fore, needless to say, the observing portion 10B5 fixed to the observing portion holding portion 10B6 fixed to the contact portion support portion 10B3 vibrates synchronously with the heart 50.

In the present modification, the image photographed by the observing portion 10B5 vibrating synchronously with the heart 50 as described above is reproduced and output by the camera display unit 6. That is, according to the present modification, there can be provided the operating field securing device which produces an effect similar to that of the operating field securing device according to the above embodiment and which can observe the behavior of a procedure subjected to the heart 50 by the manipulator portion 10B2 without being bothered by blurring due to the vibration of the heart 50.

Furthermore, the above embodiment includes various stages of inventions, and various inventions can be extracted by an appropriate combination of a plurality of disclosed constituent requirements. For example, even in a case where several constituent requirements are removed from all the constituent requirements described in the embodiment, when the problem described in the paragraphs of the problem to be solved by the invention can be solved, and the effect described in the paragraphs of the effect of the present invention is obtained, it is possible to extract, as the invention, a constitution from which the constituent requirements have been removed.

What is claimed is:

1. An operating field securing device which secures an operating field when an internal organ is subjected to a predetermined procedure, the operating field securing device including:
    a contact portion adapted to come in contact with the internal organ;
    a contact portion support portion which supports the contact portion provided at one end of the contact portion support portion;
    a manipulator portion adapted to subject the internal organ to the predetermined procedure;
    a manipulator holding portion fixed to the contact portion support portion,
    wherein the manipulator holding portion, adapted to fix relative positions of the internal organ and the manipulator portion, synchronizes a movement of the contact portion corresponding to a movement of the internal organ via the contact portion support portion, thereby holding the manipulator portion;
    an observing portion adapted to photograph a region subjected to various procedures by the manipulator portion; and
    an observing portion holding portion fixed to the contact portion support portion,
    wherein the observing portion holding portion is adapted to fix the relative positions of the internal organ and the observing portion, and synchronizes the movement of the contact portion corresponding to the movement of the internal organ via the contact portion support portion, thereby holding the observing portion.

2. The operating field securing device according to claim 1, wherein the manipulator holding portion is fixed to the contact portion.

* * * * *